US005800805A

United States Patent [19]

Salas

[11] Patent Number: 5,800,805
[45] Date of Patent: Sep. 1, 1998

[54] AEROSOL DEODORANT PRODUCT

[75] Inventor: Lucia Salas, North Bergen, N.J.

[73] Assignee: Church & Dwight Co., Inc, Princeton, N.J.

[21] Appl. No.: 878,763

[22] Filed: Jun. 19, 1997

[51] Int. Cl.$^6$ ................ A61K 7/32; A61K 7/00
[52] U.S. Cl. ............... 424/65; 424/400; 424/401; 424/484; 424/493; 424/717; 514/777; 514/778; 514/951; 423/265; 423/267; 423/275; 423/422
[58] Field of Search ............... 424/65, 400, 401, 424/484, 493, 717; 514/777, 778, 951; 423/265, 267, 275, 422

[56] References Cited

U.S. PATENT DOCUMENTS

| | | | |
|---|---|---|---|
| 3,088,874 | 5/1963 | Geary et al. | 167/32 |
| 3,317,372 | 5/1967 | Hart | 167/14 |
| 3,920,807 | 11/1975 | Curry et al. | 424/46 |
| 3,968,203 | 7/1976 | Spitzer et al. | 424/47 |
| 4,045,548 | 8/1977 | Luedders et al. | 424/47 |
| 4,183,911 | 1/1980 | Smithies et al. | 424/36 |
| 4,278,658 | 7/1981 | Hooper et al. | 424/65 |
| 4,352,789 | 10/1982 | Thiel | 424/46 |
| 4,382,079 | 5/1983 | Marschner | 424/65 |
| 4,450,151 | 5/1984 | Shinozawa | 424/46 |
| 4,534,962 | 8/1985 | Marschner | 424/65 |
| 4,548,808 | 10/1985 | Chavkin | 424/47 |
| 4,659,560 | 4/1987 | Bews et al. | 424/47 |
| 4,675,177 | 6/1987 | Geary | 424/47 |
| 4,695,451 | 9/1987 | Straw et al. | 424/47 |
| 4,740,366 | 4/1988 | Winston et al. | 424/45 |
| 4,743,440 | 5/1988 | Callingham et al. | 424/46 |
| 4,822,602 | 4/1989 | Sabatelli | 424/65 |
| 4,832,945 | 5/1989 | Osipow et al. | 424/65 |
| 4,840,786 | 6/1989 | Johnson et al. | 424/43 |
| 4,851,212 | 7/1989 | Winston et al. | 424/45 |
| 4,863,721 | 9/1989 | Beck et al. | 424/47 |
| 4,889,711 | 12/1989 | Kai et al. | 424/47 |
| 4,904,463 | 2/1990 | Johnson et al. | 424/44 |
| 4,935,224 | 6/1990 | Russo et al. | 424/47 |
| 5,114,717 | 5/1992 | Kuznitz et al. | 424/401 |
| 5,156,833 | 10/1992 | Osugi et al. | 424/46 |
| 5,156,834 | 10/1992 | Beckmeyer et al. | 424/47 |
| 5,178,871 | 1/1993 | Thill | 424/405 |
| 5,194,262 | 3/1993 | Goldberg et al. | 424/401 |
| 5,281,409 | 1/1994 | Thayer et al. | 424/47 |
| 5,368,842 | 11/1994 | Lederman et al. | 424/47 |
| 5,585,093 | 12/1996 | Murphy et al. | 424/65 |
| 5,614,179 | 3/1997 | Murphy et al. | 424/65 |
| 5,628,990 | 5/1997 | Murphy et al. | 424/65 |
| 5,631,013 | 5/1997 | Bergmann et al. | 424/401 |

FOREIGN PATENT DOCUMENTS

| | | |
|---|---|---|
| 0 485 012 A1 | 10/1991 | European Pat. Off. . |
| 1476117 | 6/1975 | United Kingdom . |

*Primary Examiner*—Shelley A. Dodson
*Attorney, Agent, or Firm*—Irving Fishman

[57] ABSTRACT

This invention provides a deodorant composition in a dispensing container which is pressurized with an aerosol propellant. The primary ingredients of a typical product are particulate sodium bicarbonate, ethanol, volatile silicone oil and a suspending agent such as hydrophobic hectorite clay. An invention aerosol deodorant product has a stable particulate sodium bicarbonate suspension phase, and exhibits excellent fluid evacuation properties with a relatively high content of ethanol and low content of aerosol propellant.

17 Claims, No Drawings

AEROSOL DEODORANT PRODUCT

BACKGROUND OF THE INVENTION

This invention generally relates to cosmetic deodorant products. More specifically this invention relates to nonaqueous aerosol deodorant compositions having a bicarbonate salt content. Sodium bicarbonate long has been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, the development of a practical and effective composition in cosmetic product form which has a deodorization capacity, and which is capable of consumer acceptability, presents many factors which are unique. Because sodium and potassium bicarbonate have only limited solubility in water, alcohol and other solvents, the preparation of a composition suitable for dispensing in cosmetic product form has involved many processing obstacles. In addition to the problem of limited solubility, sodium bicarbonate often is incompatible with other ingredients of conventional cosmetic formulations.

Other limiting factors are described in references such as U.S. Pat. No. 4,534,962. Sodium bicarbonate in solution undergoes persistent degradation into carbon dioxide and sodium carbonate (a known skin irritant). Because alkali metal bicarbonate has solubility limitations, a proportionally larger amount of water is required for higher bicarbonate salt levels in cosmetic products. Consequently less alcohol is permitted, which results in a cool wet feel on skin, and slow drying of an applied cosmetic product.

Other product developments include aerosol suspensions which are sprayed from a pressurized container having a content of particulate sodium bicarbonate slurried with a liquid propellant medium. Alkali metal bicarbonate in a propellant-soluble vehicle such as ethanol (0.3–15 weight percent) with about 90% propellant is described in British Patent 1,476,117.

The difficulties encountered with aerosol suspensions of sodium or potassium bicarbonate include the settling and/or agglomeration of the particulate suspension phase, clogging of the dispensing nozzle, a non-uniform spray pattern, nonadherence of the particulate bicarbonate deodorant to the sprayed skin area, and an overly wet spray which requires an extended drying time.

There is continuing interest in the development of cosmetic products which have a high level of consumer acceptance.

Accordingly, it is an object of this invention to provide a cosmetic product which is composed of a nonaqueous liquid vehicle having an effective deodorizing content of particulate alkali metal bicarbonate.

It is another object of this invention to provide an aerosol deodorant composition which is a liquid medium blend of organic solvent and propellant, and which has a suspension phase of particulate alkali metal bicarbonate with improved dimensional stability and anti-valve clogging properties.

Other objects and advantages of the present invention shall become apparent from the accompanying description and examples.

DESCRIPTION OF THE INVENTION

One or more objects of the present invention are accomplished by the provision of a deodorant composition in an aerosol dispensing container which comprises (1) between 16–43 weight percent of ethanol; (2) between about 1–15 weight percent of particulate alkali metal bicarbonate having an average particle size between about 5–100 microns; (3) between about 20–60 weight percent of volatile oil; (4) between about 0.5–3 weight percent of particulate suspending agent; and (5) between about 8–50 weight percent of aerosol propellant.

An invention aerosol deodorant product normally is in a substantially anhydrous state, since the presence of water tends to destabilize the particulate suspension phase, in addition to other disadvantages elaborated herein.

The ethanol ingredient is soluble in the aerosol liquid propellant medium, and the ethanol content is relatively high relative to the propellant content. A low volume of propellant is desirable in an aerosol product because of environmental considerations.

Besides a cost advantage, a high level of ethanol in an invention aerosol deodorant product provides a spray which has a desirable dry feel on an applied skin area. The ethanol is not a "wet" medium and it evaporates more rapidly than water.

As demonstrated in the following Examples, the quantity of ethanol can be increased to an upper limit of 43 weight percent of the aerosol deodorant composition. If the ethanol content is increased above 43 weight percent, the particulate suspension phase tends to destabilize, and there is an increased settling of the suspended particles.

A deodorizing effective quantity of particulate alkali metal bicarbonate is suspended in the aerosol liquid medium. The alkali metal bicarbonate preferably is sodium or potassium bicarbonate or a mixture thereof.

The bicarbonate salt ingredient typically can have an average particle size between about 5–100 microns. In a preferred embodiment the bicarbonate ingredient is in micronized form, and has an average particle size between about 5–20 microns.

The present invention also contemplates the use of alkali metal bicarbonate in the form of particles which are encapsulated with an organic surface coating. An invention aerosol deodorant product can have a suspension phase which contains both encapsulated and unencapsulated particles of alkali metal bicarbonate. The said bicarbonate mixture provides both immediate and long term deodorizing activities when sprayed on the underarm surface of a human subject.

The alkali metal bicarbonate core matrix of organic-encapsulated particles is sodium bicarbonate or potassium bicarbonate or a mixture thereof. The average particle size of the encapsulated alkali metal bicarbonate ingredient can range between about 20–200 microns. The organic encapsulant of the coated particles typically comprises between about 5–60 weight percent of the encapsulated alkali metal bicarbonate particles.

The organic encapsulant of the coated particles is selected from hydrophilic and hydrophobic (water-insoluble) film-forming agents, and mixtures thereof, such as hydrocolloids and polysaccharides.

The term "hydrophilic" as employed herein refers to an encapsulant film-forming agent which has a water-solubility of at least about two grams per one hundred grams of water at 25° C.

The organic encapsulant can consist of 100% hydrophilic encapsulant, or 100% water-insoluble encapsulant, or any mixture thereof. The rate of alkali metal bicarbonate release after aerosol spraying on a skin surface is directly related to the hydrophilicity of the encapsulant coating on the alkali metal bicarbonate particles. A hydrophilic encapsulant coating will sustain-release the core alkali metal bicarbonate content at a faster rate than a water-insoluble encapsulant coating. An organic encapsulant can comprise a hydrophilic polymer having a content between about 5–80 weight percent of a water-insoluble polymer.

Suitable hydrophilic encapsulants for coating the alkali metal bicarbonate particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene oxide, polyvinyl alcohol/acetate, and the like. Polyvinyl acetate is illustrative of a water-insoluble polymer which can be included as an additional coating component to moderate the hydrophilicity of a hydrophilic polymer coating.

Suitable water-insoluble encapsulants include polyvinyl acetate, polyacrylamide, polyvinyl chloride, polystyrene, polyethylene, polyurethane, polymethacrylate, paraffin wax, carnauba wax, beeswax, stearyl alcohol, zein, shellac, edible fat, and the like.

The encapsulant can be applied to the alkali metal bicarbonate particles by conventional coating means, such as rotating disk, fluidized bed, spray drying, freeze drying, tumbling, coacervation, and the like.

The volatile oil ingredient of an invention aerosol deodorant product preferably is selected from silicone and branched-chain hydrocarbon compounds.

A volatile silicone oil ingredient can be a cyclic or linear polydimethylsiloxane containing between about 3–9 silicon atoms. A suitable cyclic volatile polydimethylsiloxane compound is illustrated by the formula:

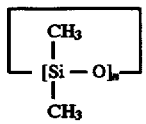

where n is an integer with a value of about 3–7.

A suitable linear polydimethylsiloxane is illustrated by the formula:

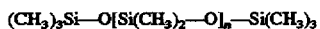

where n is an integer with a value of about 1–7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3–6. Dow Corning 245 Fluid (Dow Corning) is a cyclic volatile silicone which is commercially available. CTFA Cosmetic Ingredient Dictionary, Third Edition, (Estrin et al., Editors; The Cosmetic, Toiletry and Fragrance Association, Inc.; 1982) lists cyclic silicones on page 60, under the entry "Cyclomethicone".

A volatile hydrocarbon oil type of ingredient preferably is a $C_{12}$–$C_{20}$ branched-chain hydrocarbon compound or mixture. Suitable volatile branched-chain hydrocarbon oils include isododecane ($C_{12}$), isohexadecane ($C_{16}$), isoeicosane ($C_{20}$), and the like. These types of branched-chain hydrocarbons are marketed by Permethyl Corporation under tradenames such as Permethyl 99A, Parmethyl 101A and Permethyl 102A.

Another essential ingredient of an invention aerosol deodorant composition is between about 0.5–3 weight percent of a suspending agent in particle form.

Suitable suspending agents include colloidal silica such as pyrogenic silica having a particle size range between about 0.001–0.03 micron; colloidal alumina; hydrophobic powders such as montmorillonite clays (e.g., bentonites and hectorites) which are surface-treated with a cation surfactant such as ditallow dimethyl ammonium chloride (e.g., quaternium 18 hectorite; Bentone 38 by Rheox, Inc.).

Other suitable suspending agents are described in publications such as British 1,476,117; U.S. Pat. No. 4,045,548; and U.S. Pat. No. 4,904,463; incorporated by reference.

The propellant ingredient of an invention aerosol deodorant composition is a liquified normally-gaseous medium preferably selected from the group consisting of hydrocarbons and halogenated hydrocarbons and mixtures thereof. A typical aerosol propellant is one selected from the group consisting of $C_3$–$C_5$ aliphatic hydrocarbons and mixtures thereof.

Suitable aerosol propellants are described in publications such as U.S. Pat. Nos. 3,968,203; 4,889,711; 4,935,224; 5,156,833; 5,156,834; 5,281,409; and 5,368,842; incorporated by reference.

A present invention aerosol deodorant product can include other ingredients such as fragrances, bacteriostats, fungistats, emollients, colorants, antiinflammatory agents, antioxidants, and the like.

For example, between about 0.01–0.5 weight percent of a bacteriostat can be included as an optional ingredient. The bacteriostat functions as a deodorant by preventing bacterial generation of malodorous degradation byproducts from perspiration. Typical bacteriostatic compounds include Triclosan (Ciba-Geigy), Chloracel (Reheis Chemical Company), zinc phenolsulfonate, dichloro-m-xylenol, sodium N-lauroyl sarcosine, and the like.

Between about 0.1–2 weight percent of a fragrance can be included as an optional ingredient. The selected fragrance ingredient is one which does not adversely affect the dimensional stability of the aerosol deodorant product, and preferably which contributes an odorant masking effect. Fragrances typically are organic compounds of specific type structures, which include phenolic materials, essential oils, synthetic oils, aldehydes and ketones, polycyclic compounds, esters, and alcohols. Specific fragrances are illustrated by linalyl acetate, isopropyl myristate, cedryl acetate, myrcenyl acetate, and other compounds such as those listed in U.S. Pat. No. 5,114,717; incorporated by reference. The fragrance ingredient can be encapsulated with a film-forming polymer such as polyvinyl acetate.

A present invention aerosol deodorant product can be produced by blending the ingredients in a prescribed order of addition. In a general procedure, a concentrate is prepared by first mixing the volatile oil and suspending agent, and then incorporating ethanol, alkali metal bicarbonate and optional additives such as bacteriostat and fragrance ingredients. The concentrate is milled under high shear conditions, and then charged to an aerosol dispensing container. A valve is crimped to the container, and the propellant is charged to the container under pressure. Procedures for production of pressurized aerosol products are described in publications such as U.S. Pat. Nos. 4,183,911; 4,743,440; 4,935,224; and 5,178,871; incorporated by reference.

The following examples are further illustrative of the present invention. The components and specific ingredients are presented as being typical, and various modifications can be derived in view of the foregoing disclosure within the scope of the invention.

EXAMPLE I

This Example illustrates the particle size distribution of sodium bicarbonate before and after air-jet milling.

Commercial grade sodium bicarbonate (3DF, Church & Dwight) is processed by air-jet milling (Particle Size Technology, Inc.), and the particle size distribution of milled samples is determined in comparison with unmilled samples by means of a Microtrac laser-scattering particle size analyzer.

The 3DF sodium bicarbonate has an average particle size of 31.4 microns, and the micronized 3DF sodium bicarbonate has an average particle size of 9.8 microns.

The middle 80% of particle size distribution is between 15.4 and 55.8 microns for the 3DF sodium bicarbonate, and between 4.3 and 21.5 microns for the micronized form which is employed in the following Examples.

EXAMPLE II

This Example illustrates the settling properties of the particulate phase in aerosol deodorant products in accordance with the present invention.

An invention aerosol deodorant product is formulated with the following ingredients:

| | |
|---|---|
| Cyclomethicone | 48.2 |
| Bentone 27CG[1] | 0.8 |
| Ethanol | 24.0 |
| Triclosan | 0.3 |
| Sodium bicarbonate[2] | 6.2 |
| Fragrance[3] | 0.5 |
| Dymel 152a[4] | 20.0 |
| Settling rate (cm/min.) | 0.9 |

[1]hydrophobic clay; Rheox.
[2]micronized (average particle size of 9.8 microns).
[3]Fresh Scent; Takasago.
[4]1,1-difluoroethane; Dupont.

A concentrate is prepared by mixing the cyclomethicone and clay ingredients, followed by the addition of the ethanol, triclosan, sodium bicarbonate and fragrance. The admixture is milled under high shear conditions.

The concentrate blend is charged to a plastic-coated glass aerosol bottle. A valve is crimped to the glass bottle, and the propellant is added.

The invention aerosol product is highly effective for counteracting malodors when applied to the underarm of a human subject.

The settling rate of the aerosol product is measured after the fluid medium is agitated to form one phase, and the particulate suspension is allowed to settle for one minute. The settling rate is the length of the supernatant layer measured in centimeters after one minute.

The following aerosol deodorant products are prepared to illustrate the critical effect of the ethanol concentration on the stability of the particulate suspension phase in the fluid medium.

| INGREDIENTS | A | B | C |
|---|---|---|---|
| Cyclomethicone | 33.2 | 29.2 | 28.2 |
| Bentone 27CG | 0.8 | 0.8 | 0.8 |
| Ethanol | 39.0 | 43.0 | 44.0 |
| Triclosan | 0.3 | 0.3 | 0.3 |
| Sodium bicarbonate[1] | 6.2 | 6.2 | 6.2 |
| Fragrance | 0.5 | 0.5 | 0.5 |
| Dymel 152a | 20.0 | 20.0 | 20.0 |
| Settling rate (cm/min.) | 0.8 | 0.8 | 1.8 |

[1]micronized.

Invention deodorant aerosol products A and B have a low settling rate of 0.8 centimeters per minute, while deodorant aerosol product C has a high settling rate of 1.8 centimeters per minute. Aerosol Product C has an ethanol content of 44 weight percent, which is outside the scope of the present invention aerosol product definition.

EXAMPLE III

This Example illustrates the container evacuation properties of an aerosol deodorant product in accordance with the present invention.

An invention aerosol deodorant product D is formulated with the following ingredients:

| INGREDIENTS | D | E |
|---|---|---|
| Cyclomethicone | 35.2 | 0 |
| Bentone 27CG | 0.8 | 29.6 |
| Ethanol | 43.0 | 13.4 |
| Triclosan | 0.3 | 0.3 |
| Sodium bicarbonate[1] | 6.2 | 6.2 |
| Fragrance | 0.5 | 0.5 |
| Propellant A-85[2] | 14.0 | 50.0 |
| Can evacuation | 1.6 g remain | 50 g remain |

[1] micronized.
[2] propane/isobutane (64/36); Diversified CPC International.

Following the procedure of Example II, the cyclomethicone and clay are mixed, followed by the addition of the ethanol, triclosan, sodium bicarbonate and fragrance. The admixture is milled under high shear conditions.

The prepared concentrate blend is charged to a standard aerosol can. A valve is mounted and crimped on the can, and the propellant is added to provide invention deodorant aerosol product D.

Aerosol product D is highly effective for counteracting malodors when applied to the underarm of a human subject.

Following the same procedure, aerosol deodorant product E is prepared which is not within the scope of the present invention.

The can evacuation value for aerosol product D and aerosol product E is determined by shaking each tared can, and spraying out the can contents until the spraying action ceases. Each can then is reweighed to determine the amount of residual product in each can.

Invention aerosol deodorant product D has a residual can content of 1.6 grams, while noninvention aerosol product D has a residual can content of 50 grams. Consumer aerosol products typically have a residual can content of about 2 grams after can evacuation.

What is claimed is:

1. A deodorant composition in an aerosol dispensing container which comprises (1) between 16–43 weight percent of ethanol; (2) between about 1–15 weight percent of particulate alkali metal bicarbonate having an average particle size between about 5–100 microns; (3) between about 20–60 weight percent of volatile oil; (4) between about 0.5–3 weight percent of particulate suspending agent; and (5) between about 8–50 weight percent of aerosol propellant.

2. A deodorant composition in accordance with claim 1 wherein the alkali metal bicarbonate is sodium bicarbonate or potassium bicarbonate or a mixture thereof.

3. A deodorant composition in accordance with claim 1 wherein the alkali metal bicarbonate particles are encapsulated with an organic surface coating.

4. A deodorant composition in accordance with claim 1 wherein the alkali metal bicarbonate particles are encapsulated with a surface coating selected from the group consisting of hydrophilic and hydrophobic film-forming organic ingredients.

5. A deodorant composition in accordance with claim 1 wherein the alkali metal bicarbonate particles are encapsulated with a polysaccharidic surface coating.

6. A deodorant composition in accordance with claim 1 wherein the alkali metal bicarbonate ingredient is a mixture of encapsulated and unencapsulated particles.

7. A deodorant composition in accordance with claim 1 wherein the volatile oil is selected from the group consisting of silicone and branched-chain hydrocarbon compounds.

8. A deodorant composition in accordance with claim 1 wherein the volatile oil ingredient comprises a cyclic or linear polydimethylsiloxane containing 3–9 silicon atoms.

9. A deodorant composition in accordance with claim 1 wherein the volatile oil ingredient comprises a $C_{12}$–$C_{20}$ branched-chain hydrocarbon.

10. A deodorant composition in accordance with claim 1 wherein the suspending agent is selected from the group consisting of colloidal clay and silica.

11. A deodorant composition in accordance with claim 1 wherein the suspending agent is hydrophobic surface-treated bentonite clay.

12. A deodorant composition in accordance with claim 1 wherein the suspending agent is hydrophobic surface-treated hectorite clay.

13. A deodorant composition in accordance with claim 1 wherein the suspending agent is pyrogenic silica.

14. A deodorant composition in accordance with claim 1 wherein the aerosol propellant is a liquified normally-gaseous medium selected from the group consisting of hydrocarbons and halogenated hydrocarbons and mixtures thereof.

15. A deodorant composition in accordance with claim 1 wherein the aerosol propellant is selected from the group consisting of $C_3$–$C_5$ aliphatic hydrocarbons and mixtures thereof.

16. A deodorant composition in accordance with claim 1 which contains between about 0.01–0.5 weight percent of bacteriostat as an optional ingredient.

17. A deodorant composition in accordance with claim 1 which contains between about 0.1–2 weight percent of fragrance as an optional ingredient.

* * * * *